United States Patent
Heinze et al.

(10) Patent No.: US 11,090,388 B2
(45) Date of Patent: Aug. 17, 2021

(54) DIALYSIS SOLUTION HAVING AT LEAST ONE OSMOTIC AGENT

(71) Applicants: FRESENIUS MEDICAL CARE DEUTSCHLAND GMBH, Bad Homburg (DE); FRIEDRICH-SCHILLER-UNIVERSITAET JENA, Jena (DE)

(72) Inventors: Thomas Heinze, Jena (DE); Robert Hampe, Jena (DE); Robert Berlich, St. Wendel (DE); Lisa Finkler, Nonnweiler (DE); Jens Lothar Burkhart, St. Ingbert (DE)

(73) Assignees: FRESENIUS MEDICAL CARE DEUTSCHLAND GMBH, Bad Homburg (DE); FRIEDRICH-SCHILLER-UNIVERSITAET JENA, Jena (DE)

( * ) Notice: Subject to any disclaimer, the term of this patent is extended or adjusted under 35 U.S.C. 154(b) by 0 days.

(21) Appl. No.: 15/775,956

(22) PCT Filed: Nov. 14, 2016

(86) PCT No.: PCT/EP2016/001898
§ 371 (c)(1),
(2) Date: May 14, 2018

(87) PCT Pub. No.: WO2017/080675
PCT Pub. Date: May 18, 2017

(65) Prior Publication Data
US 2018/0326075 A1    Nov. 15, 2018

(30) Foreign Application Priority Data
Nov. 13, 2015  (DE) .................... 10 2015 014 699.8

(51) Int. Cl.
| | | |
|---|---|---|
| *A61K 31/718* | (2006.01) | |
| *A61K 9/08* | (2006.01) | |
| *A61K 31/205* | (2006.01) | |
| *A61K 31/185* | (2006.01) | |
| *A61K 47/36* | (2006.01) | |
| *A61K 36/47* | (2006.01) | |
| *A61K 45/06* | (2006.01) | |

(52) U.S. Cl.
CPC ................ *A61K 47/36* (2013.01); *A61K 9/08* (2013.01); *A61K 31/185* (2013.01); *A61K 31/205* (2013.01); *A61K 31/718* (2013.01); *A61K 36/47* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2,580,352 A | 12/1951 | Grassie | |
| 2,883,378 A | 4/1959 | Wettstein et al. | |
| 4,016,354 A * | 4/1977 | Greenwood | C08B 31/12 536/111 |
| 4,668,396 A | 5/1987 | Baurmeister et al. | |
| 6,284,140 B1 * | 9/2001 | Sommermeyer | A61K 31/715 210/646 |
| 6,822,002 B1 * | 11/2004 | Arduini | A61K 31/205 435/128 |
| 2012/0295873 A1 | 11/2012 | Guerin-Deremaux et al. | |

FOREIGN PATENT DOCUMENTS

| | | |
|---|---|---|
| DE | 102004023828 | 12/2005 |
| DE | 102010012281 | 9/2011 |
| DE | 102010012282 | 9/2011 |
| EP | 0602585 | 6/1994 |
| KR | 20140092593 | * 7/2014 |
| WO | WO 2004/022602 | 3/2004 |

OTHER PUBLICATIONS

Ryu, Hye Myung et al., Machine language translation of KR 2014-0092593, "Osmotic agent for peritoneal dialysis comprising starch sulfate and composition for peritoneal dialysis comprising of it", obtained from Google on Feb. 1, 2019. (Year: 2014).*
Liang, H.-C. et al., Green Chemistry, "Syntheses of water-soluble N-donor ligands for aqueous catalysis using green, Michael-type addition reactions", 2005, vol. 7, pp. 410-412 (Year: 2005).*
PubChem, "2-hydroxethyl starch", PubChem CID: 16213095; available at https://pubchem.ncbi.nlm.nih.gov/compound/16213095; website modified date: Jun. 6, 2020. (Year: 2020).*

* cited by examiner

*Primary Examiner* — Bahar Craigo
(74) *Attorney, Agent, or Firm* — Jacobson Holman PLLC (57) ABSTRACT

The invention relates to a dialysis solution having at least one osmotic agent, with the osmotic agent being a polysaccharide modified by 2-sulfoethyl groups.

15 Claims, 11 Drawing Sheets

DIALYSIS SOLUTION HAVING AT LEAST ONE OSMOTIC AGENT

The present invention relates to a dialysis solution having at least one osmotic agent.

Dialysis solutions such as are used in peritoneal dialysis, hemodialysis, hemodiafiltration, etc. are known in a number of different compositions.

DE 10 2004 023 828 A1, for example, discloses a solution for a peritoneal dialysis which contains, in addition to electrolytes, an osmotic agent in the form of glucose.

The glucose serving as an osmotic agent has the result that the transport of water via the membrane is accelerated and that the ultrafiltration rate is thus improved. A further known osmotic agent is icodextrin which is a starch-derived branched glucose polymer.

It is the underlying object of the present invention to further develop a dialysis solution such that its ultrafiltration performance is increased with respect to known dialysis solutions.

This object is achieved by a dialysis solution having the features of claim 1. Provision is accordingly, made that the osmotic agent is a polysaccharide that is modified by 2-sulfoethyl groups It has surprisingly been found that polysaccharides that are modified by 2-sulfoethyl groups have a very high effectivity in use as osmotic agents.

The modification takes place at the free hydroxyl groups of the polysaccharide. The 2-sulfoethyl groups have the chemical formula —$CH_2$—$CH_2$—S(=O)(=O)OR, where R represents hydrogen or a hydrocarbon residue having, for example, 1 to 10 carbon atoms and is preferably hydrogen.

In a further embodiment, R is a cation, for example sodium or potassium, so that the sulfoethyl starch is present as salt, preferably as sodium salt.

In an embodiment, the modified polysaccharide is a 2-sulfoethyl starch.

Starches of various sources (e.g. from potatoes, corn, manioc (tapioca), rice, peas, wheat and further types of grain) as well as specific starch types such as Hylon VII, amioca powder or waxy corn starch) are conceivable as starting materials for the preparation of the 2-sulfoethyl starch.

It is possible to achieve a preferred substitution at position 2 or 6 through the choice of the reaction conditions. Position 3 is typically substituted less strongly than both position 2 and position 6.

In a preferred embodiment of the invention, the preparation of the modified polysaccharide takes place by the transformation of starch with sodium vinyl sulfate.

In a further preferred embodiment of the invention, the reduction of the starch takes place using sodium boron hydride before sulfoethylation.

In an embodiment, the modified polysaccharide has a degree of substitution of between 0.05, and 1.0 and preferably of between 0.2 and 9.5. The degree of substitution is defined as the average number of substituents per repeat unit of the polymer.

In an embodiment, the molar mass of the unmodified polysaccharide underlying the modified polysaccharide is between 1,000 and 50,000 g/mol and preferably between 1,000 and 20,000 g/mol.

The molar mass of the unmodified sulfoethyl starch is preferably between 1,000 and 50,000 g/mol and particularly preferably between 1,000 and 20,000 g/mol.

In an embodiment, the dialysis solution does not contain any further osmotic agent such as unmodified starch, icodextrin, or glucose in addition to the modified polysaccharide.

Alternatively, mixtures of the modified polysaccharide and additives and/or further osmotic agents such as unmodified starch, icodextrin, L-carnitine, dipeptiven, taurine, or glucose or a combination of two or more of these components is also conceivable.

In an embodiment, the dialysis solution has exactly one type of modified polysaccharide. Mixtures of a plurality of such polysaccharides are alternatively also conceivable.

In an embodiment, the modified polysaccharide is completely water-soluble.

In an embodiment, the dialysis solution furthermore contains electrolytes and a buffer system. Suitable electrolytes comprise sodium ions, potassium ions, calcium ions, magnesium ions and/or chloride ions. Suitable buffer systems comprise a lactate buffer, a hydrogen carbonate buffer, or a combination thereof. The buffer system serves the setting of a physiological pH.

The pH of the dialysis solution is preferably in the range between 5.0 and 8.0.

If it is a single-chamber bag system, the pH is preferably between 5.0 and 8.0, particularly preferably between 5.5 and 6.5.

If it is a dual-chamber bag system, the mixed pH (after the mixing of the partial solutions) is preferably between 5.0 and 8.0 and particularly preferably between 6.5 and 7.5. The pH of the acid partial solution is preferably between 3.0 and 5.0 and the pH of the base partial solution is preferably between 7.0 and 9.0.

In an embodiment, the electrolytes, where present and independently of one another, are present in the dialysis solution in the following concentrations (figures in mmol/l):

| | |
|---|---|
| Sodium ions | 125-150 |
| Potassium ions | 0-4.5 |
| Calcium ions | 0-2.5 |
| Magnesium ions | 0-5 |
| Chloride ions | 90-120 |
| Lactate/Lactic acid/(Hydrogen) carbonate/$CO_2$ | 30-60 |

The dialysis solution in accordance with the invention preferably serves a use in peritoneal dialysis. A use of the solution in accordance with the invention is alternatively also conceivable in hemodialysis or hemodiafiltration.

The present invention further relates to a method of preparing an osmotic agent of a dialysis solution by modification of a polysaccharide by 2-sulfoethyl groups. All of the above-named features can also be an element of the method, i.e. the disclosure content relating to the dialysis solution in accordance with the invention is accordingly also the disclosure content of the method in accordance with the invention.

Further details and advantages will be explained with reference to the Figures and embodiments described in the following. There are shown in the Figures:

BRIEF DESCRIPTION OF THE DRAWINGS

Figure 1:
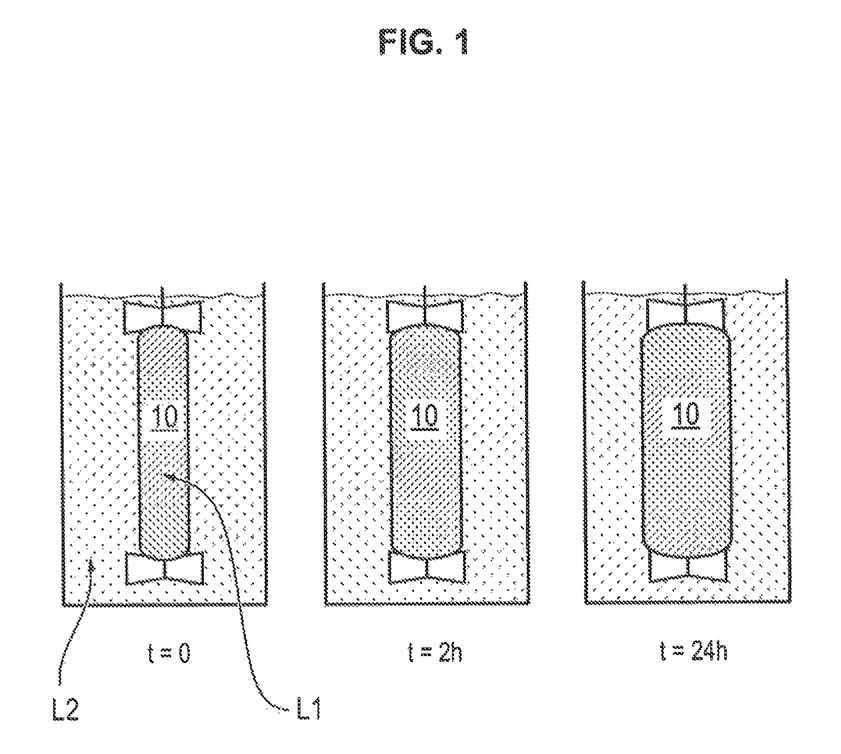
FIG. 1: schematic representations of a tube filled with the dialysis solution in accordance with the invention at different times.

FIG. 1 shows a tube 10 whose wall is formed by a semipermeable membrane. The membrane can, for example, be regenerated cellulose.

A dialysis solution L1 containing an osmotic agent is located in the interior of the tube 10. The tube 10 is located in a solution L2 which has the same composition as the solution L1 in the tube 10 with the sole difference that the solution L2 does not have any osmotic agent.

FIG. 1, left hand illustration, shows the arrangement at the time t=0, i.e. at the start of the experiment at which the filled tube 10 was placed into the solution L2.

FIG. 1, middle illustration, shows the arrangement after a two-hour dwell time (t=2 h); and FIG. 1, right hand illustration, shows the arrangement after a 24-hour dwell time (t=24 h).

As can be seen from a comparison of the illustrations of FIG. 1, water has flowed into the tube due to the osmotic effect of the solution L1 so that the volume of said tube increases accordingly over time.

Figure 2:
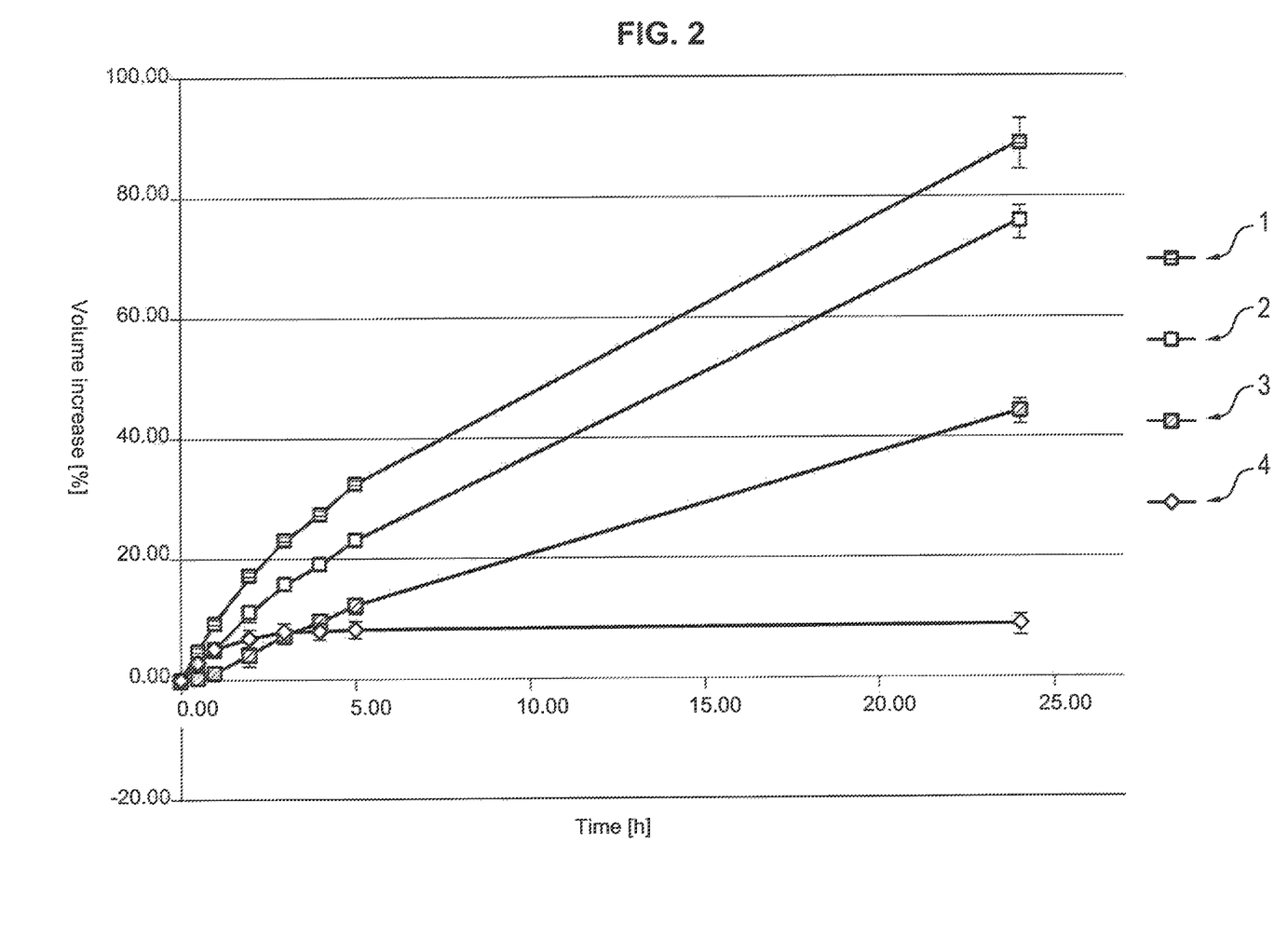
FIG. 2: developments of the volume increase for tubes filled with different dialysis solution over time.

FIG. 2 shows the volume increase in % (starting from the start of the experiment at t=0) over time for a further tube experiment for solutions having different osmotic agents. Those solutions here whose developments are provided with the reference numerals 1 and 2 have as the only osmotic agent 5% (w/v) 2-sulfoethyl starch having an average degree of substitution DS of 0.46 (solution 1) and 0.20 (solution 2), each prepared from tapioca starch (numerically mean molar mass, Mn=3321 g/mol).

Reference numerals 3 and 4 relate to solutions having 5% (w/v) glucose (solution 4) and having 5% (w/v) icodextrin (solution 3).

Figure 3:
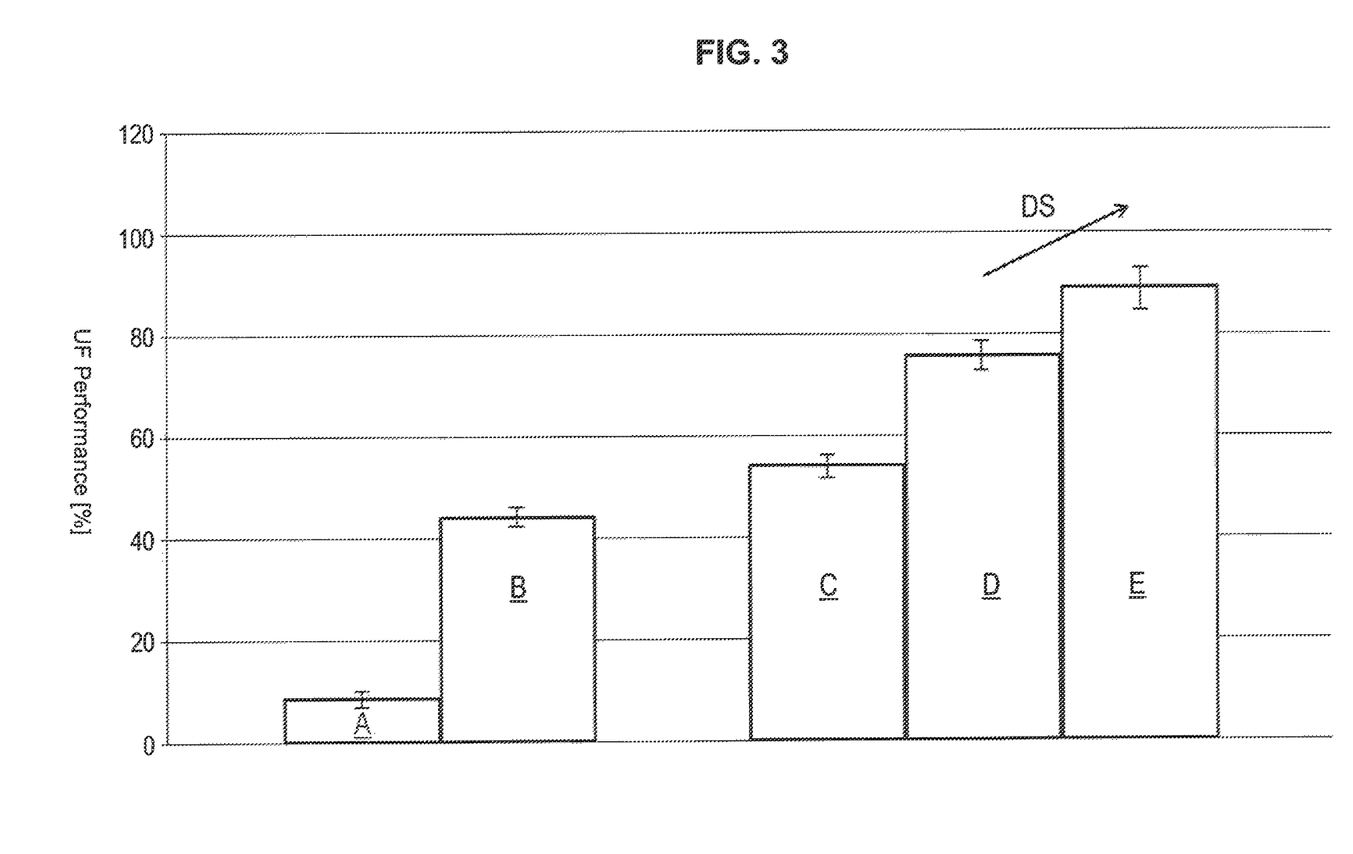
FIG. 3: a bar chart of the volume increase for tubes filled with different dialysis solution after 24 hours.

A further evaluation of the osmotic effect of known osmotic agents and of osmotic agents in accordance with the invention is shown in FIG. 3, with FIG. 3 showing the volume increase, i.e. the UF performance (UF=ultrafiltration) of the tube 10 after a 24-hour dwell time on the ordinate. The value 0% means that no volume change has resulted with respect to the start of the experiment (t=0); the value 100% means a doubling of the volume over the starting state at t=0.

The experimental conditions were identical for both FIGS. 2 and 3.

Reference symbol A shows the result for the use of 5% (w/v) glucose and illustrates the fact that a volume increase by 10% has taken place after a 24-hour dwell time. Reference symbol B shows the result for the use of a 5% (w/v) icodextrin solution, with a volume increase of 40% having taken place after a 24-hour dwell time. Reference symbol C shows the result for the use of 5% (w/v) tapioca starch (Mn=3321 g/mol), with a volume increase of a good 50% having taken place after a 24-hour dwell time.

Reference symbols D and E show the result for dialysis solutions in accordance with the present invention, with 5% w/v) 2-sulfoethyl starch being used as the only osmotic agent having an average degree of substitution DS of 0.46 (E) and 0.20 (D), each prepared from tapioca starch (numerically mean molar mass, Mn=3321 g/mol) as described in connection with FIG. 2.

It becomes clear from FIG. 3 that on the use of the osmotic agents in accordance with the invention a volume increase of up to 90% is achieved, which is considerably above what is achieved using known osmotic agents.

The experimental conditions for the results in accordance with FIGS. 2 and 3 are as follows: A filling volume of 10 ml of a liquid was filled into a tube having a semipermeable tube wall of regenerated cellulose (MWCO: 1000 Da, Carl Roth corporation). This liquid comprises an aqueous solution of the corresponding osmotic agent having a concentration of the osmotic agent of 5% (w/v), with further ingredients being present by $Ca^{2+}$ in a concentration of 1 mmol/l, $Mg^{2+}$ in a concentration of 0.5 mmol/l, $Na^+$ in a concentration of 138 mmol/l, $Cl^-$ in a concentration of 106 mmol/l and lactate in a concentration of 35 mmol/l.

This filled tube was stored while being moved at a temperature of 38° C. in a bath of the same experiment solution, but without an osmotic agent, for 24 hours.

The volume increase of the filling volume of the tube reflecting the osmotic effect of the agent was determined at different times. As can be seen from FIG. 2, the osmotic agents in accordance with the present invention were compared with known osmotic agents in the form of glucose and icodextrin.

FIG. 2 shows that the volume increase of the tube for all dialysis solutions containing 2-sulfoethyl starch is above 70% after a 24-hour dwell time. A volume increase of approximately 95% after 24 hours was achieved as the maximum value.

In contrast, the final values after 24 h for icodextrin were at a good 40% and those of glucose at approximately 10%.

The osmotic agents in accordance with the invention not only show an increased ultrafiltration efficiency after 24 hours, but also a higher value with small dwell times with respect to icodextrin.

While the volume increase with icodextrin has a substantially linear progression, a comparatively steep increase can be seen with the dialysis solutions containing 2-sulfoethyl starch, said steep increase bottoming out at higher dwell times and merging into a substantially linear progression.

The increase of the tube volume at low dwell times is comparable with that of glucose on the use of 2-sulfoethyl starch. At higher values, however, the volume increase with glucose as the osmotic agent is much smaller and remains constant after a dwell time of approximately three hours, as can be seen from FIG. 2.

Some embodiments for carrying out the invention will be described in the following:

EXAMPLE 1

Figure 4:
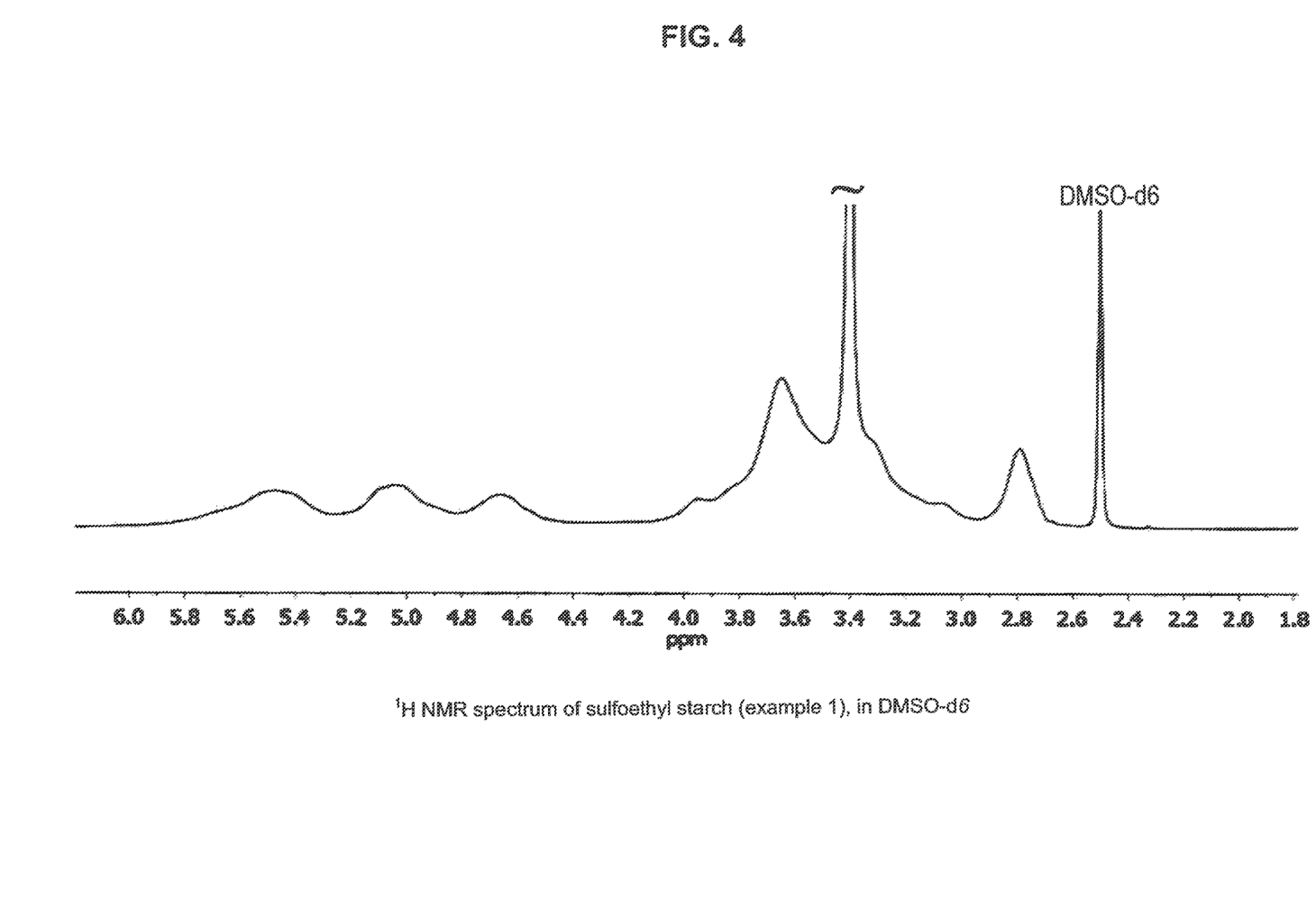
FIG. 4 describes a $^1$H NMR spectrum of sulfoethyl starch and its corresponding example (i.e., Example 1).
Figure 5:
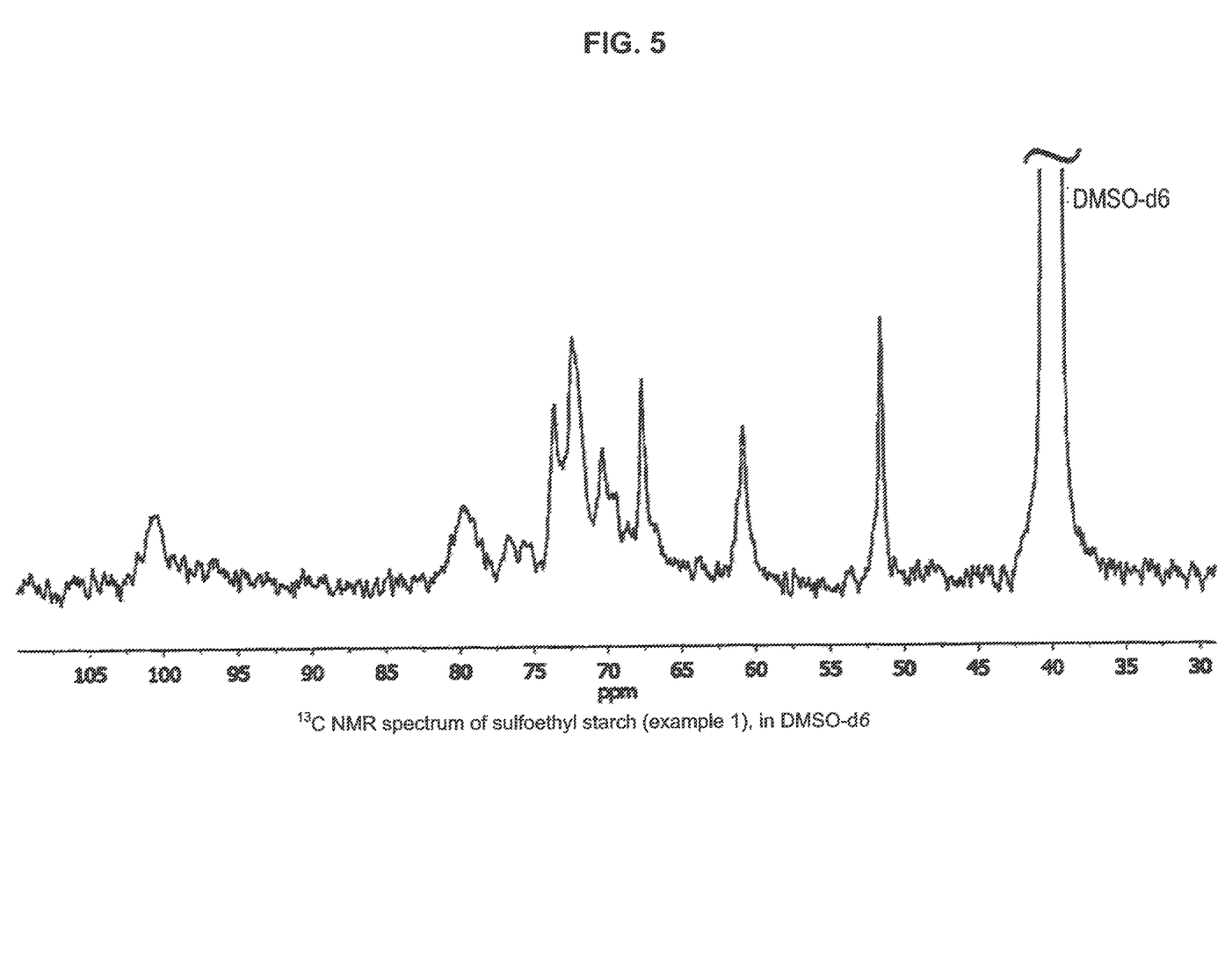
FIG. 5 describes a $^{13}$C NMR spectrum of sulfoethyl starch and its corresponding example (i.e., Example 1).

40.0 g degraded tapioca starch ($\overline{M}_n$=3.321 g/mol) in 480 mL isopropanol are admixed with 77.1 g 25% (w/v) aqueous sodium vinyl sulfonate solution (0.6 mol/mol anhydroglucose unit, AGE), in which 14.82 g NaOH have been dissolved, in a nitrogen atmosphere while stirring. The reaction mixture is heated to 80° C., is stirred for 1 h at this temperature, and subsequently 77.1 g of the sodium vinyl sulfonate solution (0.6 mol/AGE) are again added. After a further 3 h reaction time at 80° C., the mixture is cooled to room temperature and is neutralized with acetic acid. The product is precipitated in 4 L methanol, filtered, washed five times with 1 L methanol I and is reprecipitated twice from 150 mL water in 1.5 L methanol. It is dissolved in 300 mL water; the polymer solution is filtered and freeze-dried. The structural proof took place by $^1H$ and $^{13}C$ MR spectroscopy (FIGS. 4 and 5) as well as elementary analysis. Average degree of substitution (DS, determined by means of elementary analysis): 0.46.

EXAMPLE 2

Figure 6:
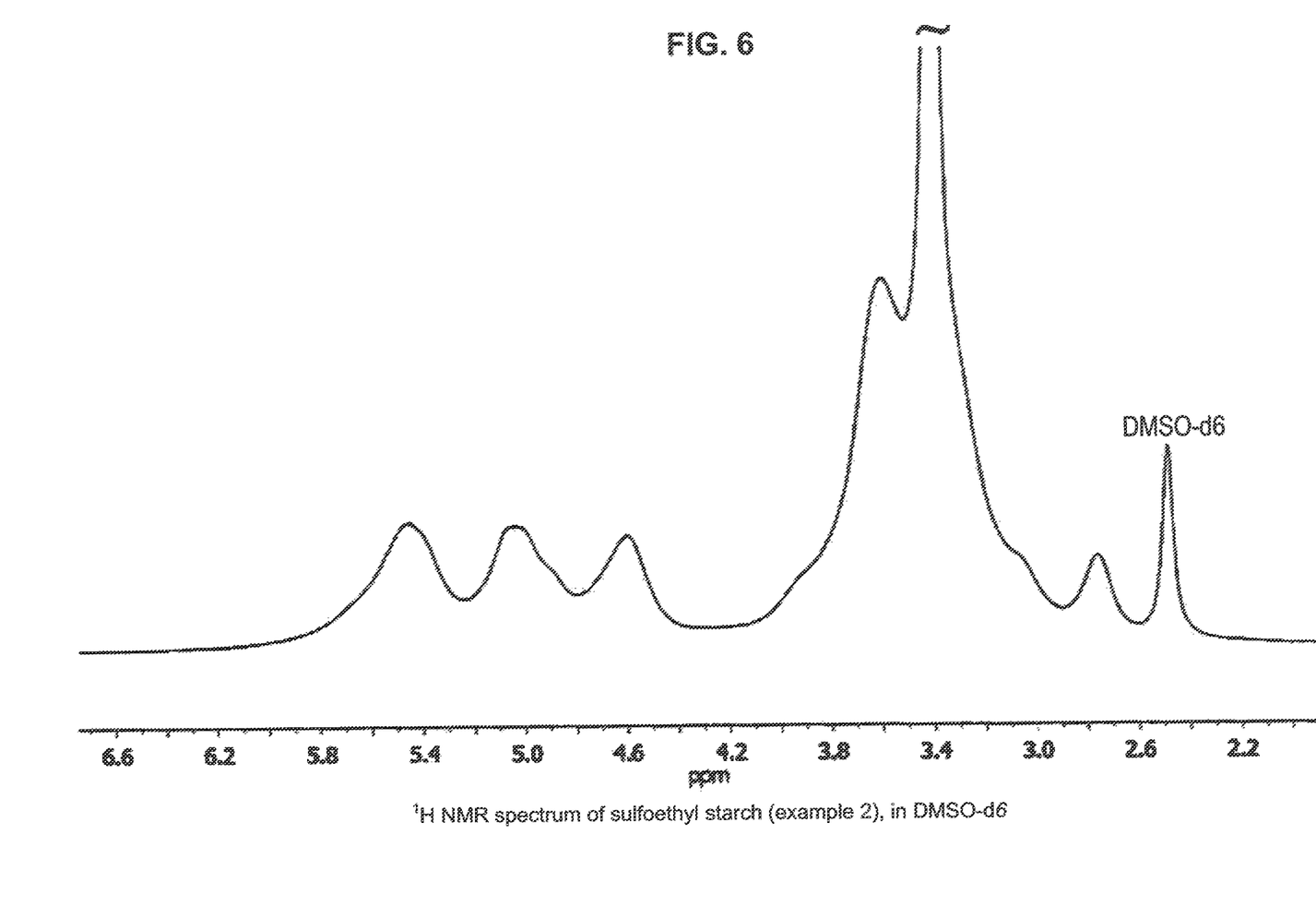
FIG. 6 describes a $^1$H NMR spectrum of sulfoethyl starch and its corresponding example (i.e., Example 2).
Figure 7:
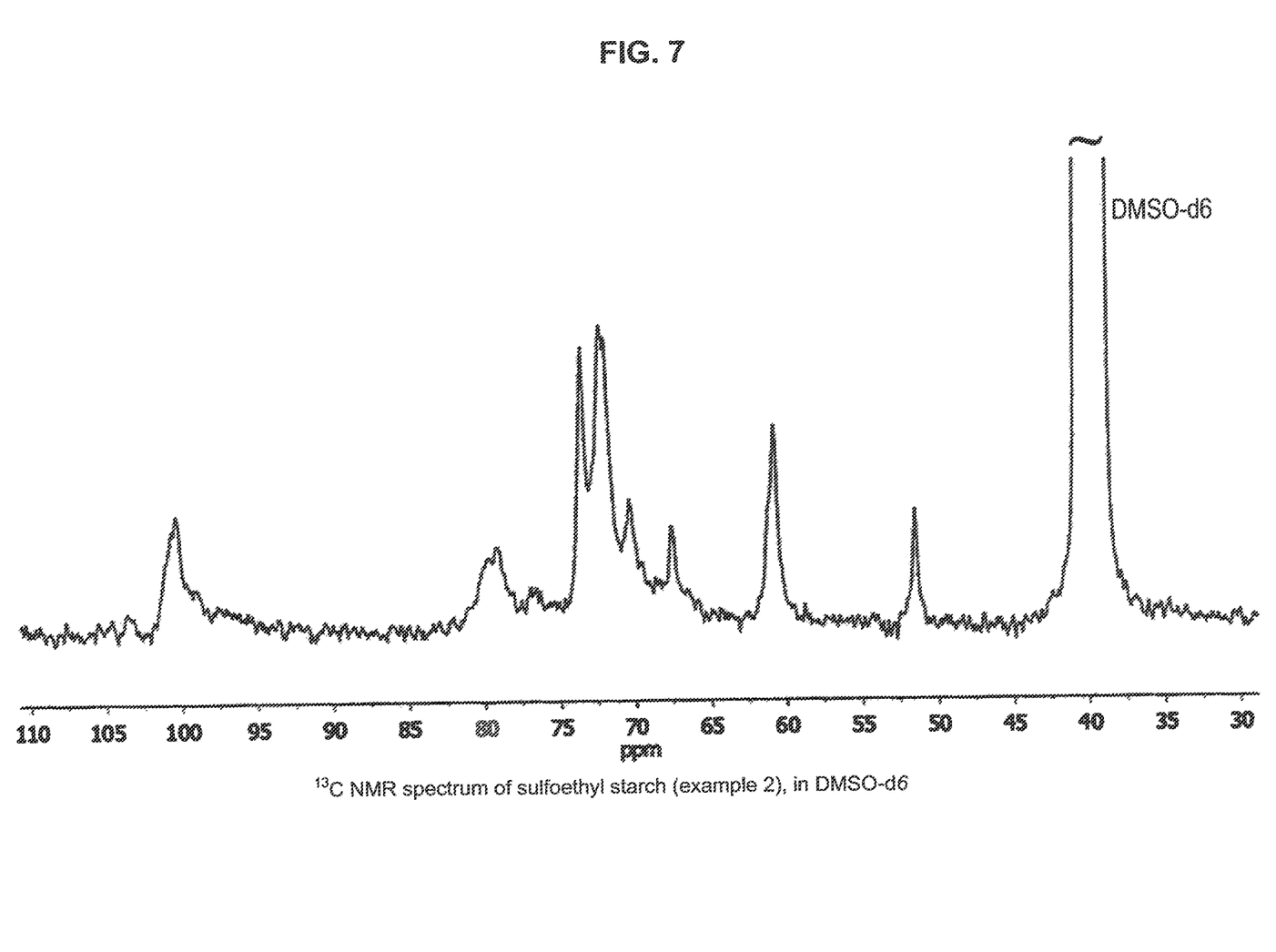
FIG. 7 describes a $^{13}$C NMR spectrum of sulfoethyl starch and its corresponding example (i.e., Example 2).

In accordance with Example 1, 40.0 g degraded tapioca starch ($\overline{M}_n$=3.321 g/mol) are converted with a total of 64.28 25% aqueous sodium vinyl sulfonate solution (0.5 mol/mol AGE) and 7.41 g NaOH. The raw product is decanted by the reaction medium, is washed three times with 500 mL methanol in each case, and is reprecipitated three times from 300 mL water in 3 L methanol. After dissolving in 300 mL water, the solution is filtered and freeze-dried. $^1H$ and $^{13}C$ NMR spectra confirm the structure (FIGS. 6 and 7).

DS (determined by means of elementary analysis): 0.20.

EXAMPLE 3

Figure 8:
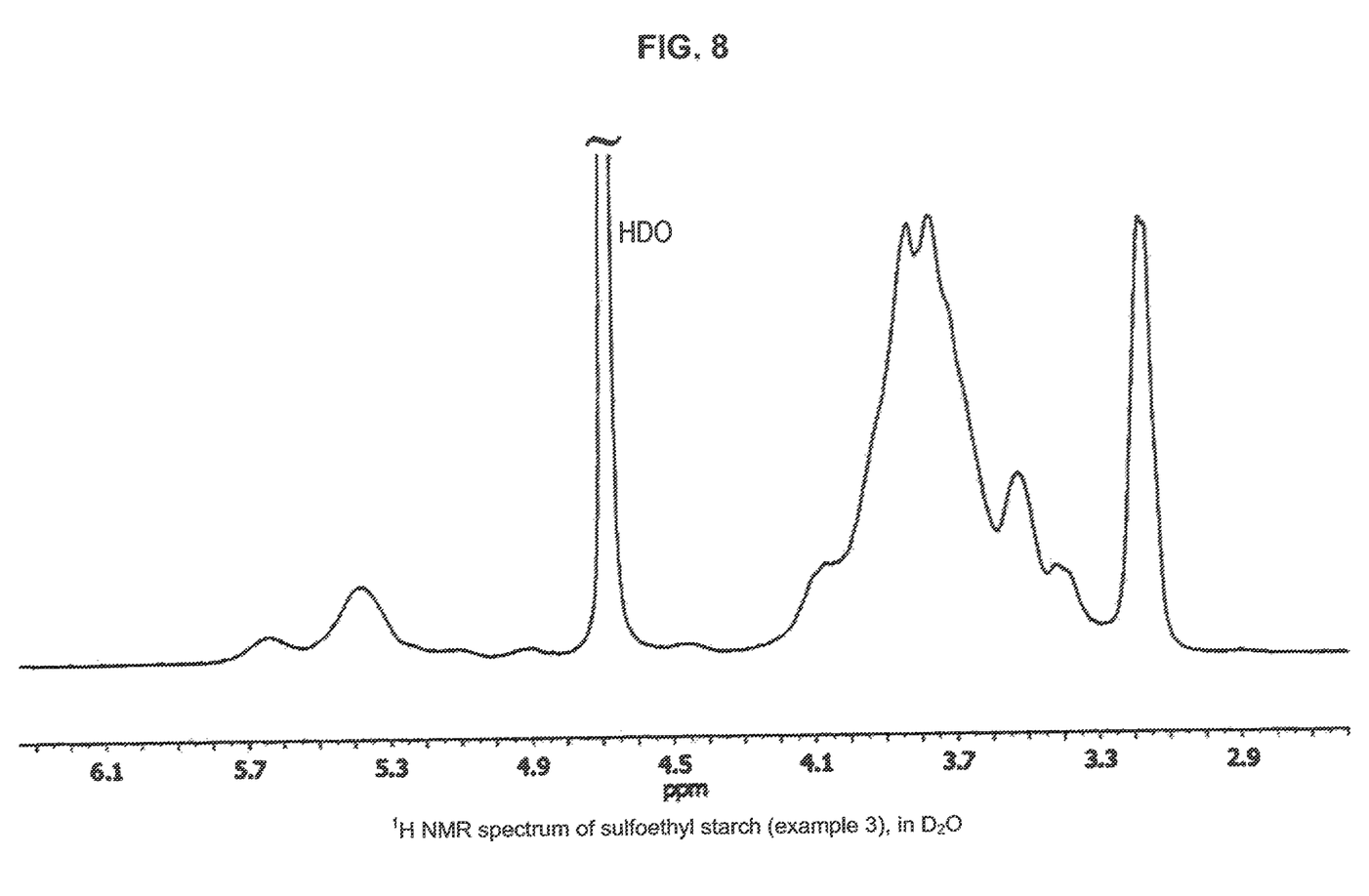
FIG. 8 describes a $^1$H NMR spectrum of sulfoethyl starch and its corresponding example (i.e., Example 3).
Figure 9:
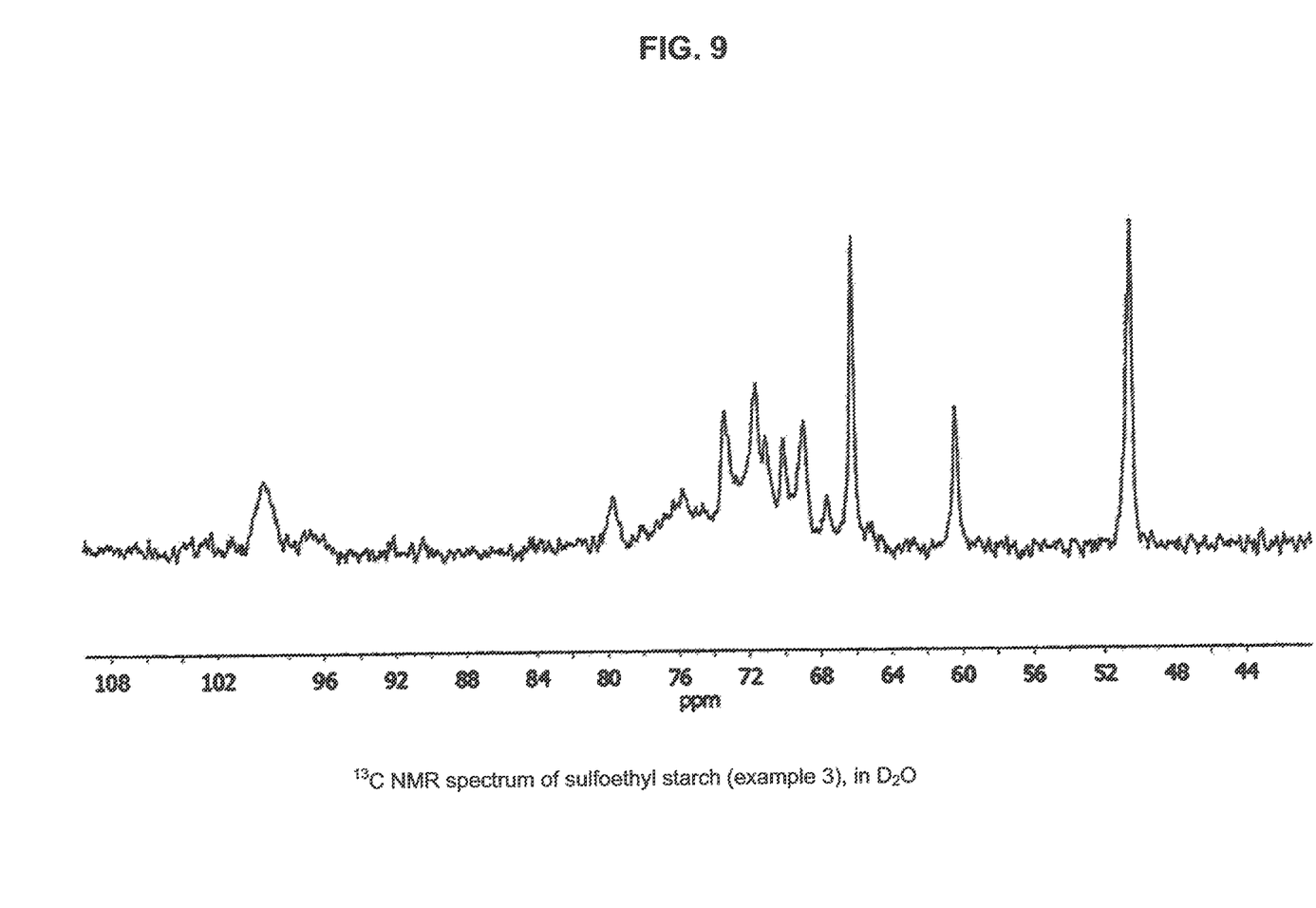
FIG. 9 describes a $^{13}$C NMR spectrum of sulfoethyl starch and its corresponding example (i.e., Example 3).

In accordance with Example 1, 40.0 g degraded tapioca starch ($\overline{M}n$=3.321 g/mol) are converted with a total of 385.64 25% (w/w) aqueous sodium vinyl sulfonate solution (3 mol/mol AGE) and 44.46 g NaOH. The obtained sulfoethyl starch is converted a second time in accordance with Example 1 after isolation (1.2 mol sodium vinyl sulfonate/mol AGE) and purified. $^1H$ and $^{13}C$ NMR spectra confirm the structure (FIGS. 8 and 9).

DS (determined by means of elementary analysis): 0.68.

EXAMPLE 4

30.0 g degraded tapioca starch ($\overline{M}n$=3.321 g/mol) are dissolved in 270 mL water at 80° C. and the solution is set to pH 8 with NaHCO$_3$. After cooling to 60° C., 1.74 g sodium boron hydride (0.25 mol/mol AGE) is added portion-wise and the solution is stirred for 24 h. The excess sodium boron is destroyed by addition of 10 mL acetone. After concentrating the solution in vacuum and filtration, the sample is dialyzed against water (membrane with a molecular weight cut-off of 2500 g/mol) and is subsequently freeze-dried.

Figure 10:
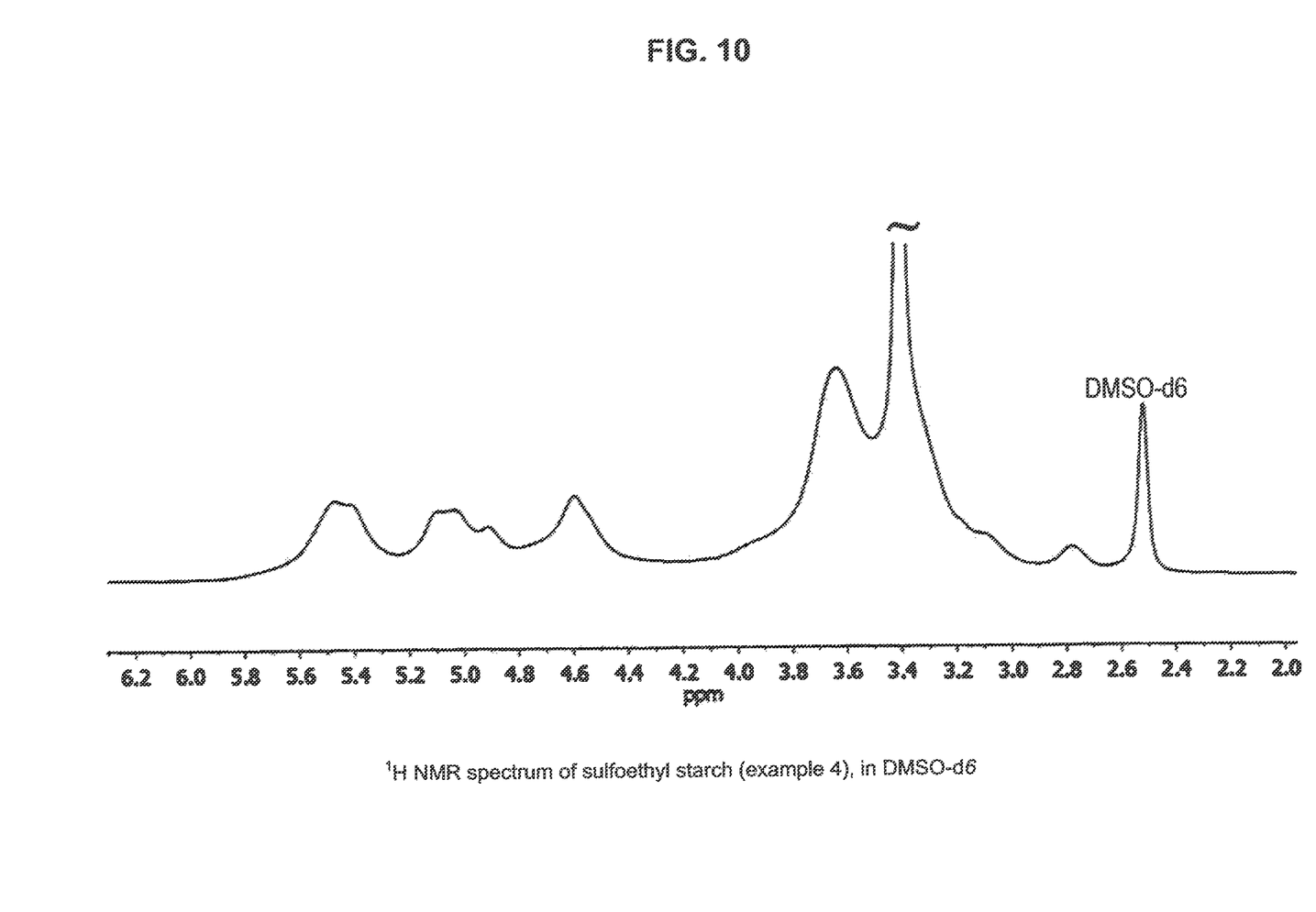
FIG. 10 describes a $^1$H NMR spectrum of sulfoethyl starch and its corresponding example (i.e., Example 4).
Figure 11:
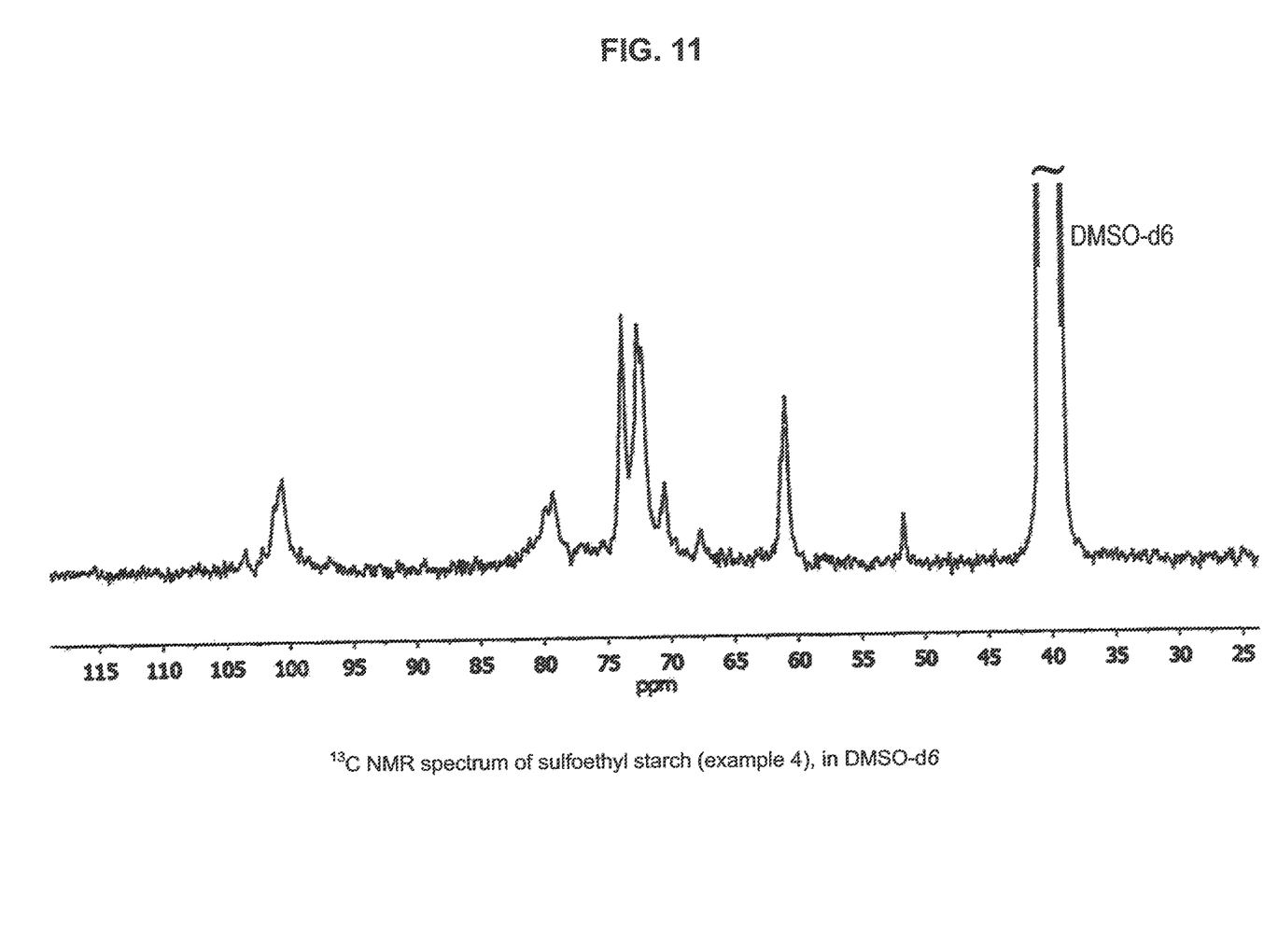
FIG. 11 describes a $^{13}$C NMR spectrum of sulfoethyl starch and its corresponding example (i.e., Example 4).

In accordance with Example 2, 25.0 g of the starch treated with sodium boron hydride is converted and isolated with a total of 40 g 25% (w/w) aqueous sodium vinyl sulfonate solution (0.5 mol/mol AGE) and 4.63 g NaOH. $^1H$ and $^{13}C$ NMR spectra confirm the structure (FIGS. 10 and 11).

DS (determined by means of elementary analysis): 0.09.

The invention claimed is:

1. A dialysis solution having at least one osmotic agent, characterized in that the osmotic agent is a modified polysaccharide, wherein the modified polysaccharide is a 2-sulfoethyl starch, characterized in that the starch underlying the 2-sulfoethyl starch is a starch that was reduced with NaBH$_4$ before the sulfoethylation, and wherein the molar mass of the unmodified sulfoethyl starch is between 1,000 and 20,000 g/mol.

2. A dialysis solution in accordance with claim 1, characterized in that the modified polysaccharide has a degree of substitution between 0.05 and 1.0.

3. A dialysis solution in accordance with claim 1, characterized in that the dialysis solution does not contain any further osmotic agent in addition to the modified polysaccharide.

4. A dialysis solution in accordance with claim 1, characterized in that the dialysis solution furthermore has electrolytes and a buffer system.

5. A dialysis solution in accordance with claim 4, characterized in that the electrolytes are selected from the group consisting of sodium ions, potassium ions, calcium ions, magnesium ions, chloride ions, and combinations thereof.

6. A dialysis solution in accordance with claim 4, characterized in that the buffer system is a lactate buffer, a hydrogen carbonate buffer, or a combination thereof.

7. A dialysis solution in accordance with claim 4, characterized in that the electrolytes, where present and independently of one another, are present in the following concentrations in the dialysis solution (figures in mmol/l):

| | |
|---|---|
| Sodium ions | 125-150 |
| Potassium ions | 0-4.5 |
| Calcium ions | 0-2.5 |
| Magnesium ions | 0-5 |
| Chloride ions | 90-120 |
| Lactate/Lactic acid/(Hydrogen) carbonate/CO$_2$ | 30-60. |

8. A dialysis solution in accordance with claim 1, characterized in that the pH of the dialysis solution is between 5.0 and 8.0.

9. A dialysis solution in accordance with claim 1 for use in peritoneal dialysis.

10. A dialysis solution in accordance with claim 1, characterized in that the modified polysaccharide has a degree of substitution between 0.2 and 0.5.

11. A dialysis solution in accordance with claim 1, characterized in that the dialysis solution comprises mixtures of the modified polysaccharide and further osmotic agents.

12. A dialysis solution in accordance with claim 1, characterized in that the dialysis solution comprises mixtures of the modified polysaccharide and (i) carnitine or (ii) taurine.

13. A dialysis solution in accordance with claim 1, characterized in that the pH of the dialysis solution is between 5.5 and 6.5.

14. A dialysis solution in accordance with claim 1, characterized in that the pH of the dialysis solution is between 6.5 and 7.5.

15. A method of preparing an osmotic agent of a dialysis solution in accordance with claim 1 comprising modification of a polysaccharide starch by 2-sulfoethyl groups.

* * * * *